US00PP32186P3

(12) United States Plant Patent
Brazelton et al.

(10) Patent No.: US PP32,186 P3
(45) Date of Patent: Sep. 15, 2020

(54) BLUEBERRY PLANT NAMED 'FCM14-052'

(50) Latin Name: *Vaccinium corymbosum*
Varietal Denomination: FCM14-052

(71) Applicant: FALL CREEK FARM & NURSERY, INC., Lowell, OR (US)

(72) Inventors: David M. Brazelton, Walterville, OR (US); Peter Stefan Boches, Hilo, HI (US); Antonio Alamo Bermudo, Seville (ES)

(73) Assignee: FALL CREEK FARM & NURSERY, INC., Lowell, OR (US)

( * ) Notice: Subject to any disclaimer, the term of this patent is extended or adjusted under 35 U.S.C. 154(b) by 0 days.

(21) Appl. No.: 16/501,387

(22) Filed: Apr. 4, 2019

(65) Prior Publication Data

US 2019/0313561 P1 Oct. 10, 2019

Related U.S. Application Data

(60) Provisional application No. 62/761,783, filed on Apr. 5, 2018.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
See application file for complete search history.

(56) References Cited

PUBLICATIONS https://extension.oreganstate.edu/crop-production/berries/how-blueberry-plants-develop-grow. Retrieved from the Internet on Jan. 14, 2020.*

* cited by examiner

*Primary Examiner* — Susan McCormick Ewoldt
(74) *Attorney, Agent, or Firm* — Panitch Schwarze Belisario & Nadel LLP

(57) ABSTRACT

The new blueberry plant variety 'FCM14-052' is provided. 'FCM14-052' is a commercial variety intended for the hand harvest fresh market. The new blueberry plant originated from a cross of 'FL01-06' (female parent, not patented) by FL06-556 (pollen parent, U.S. Pat. No. 27,771). 'FCM14-052' selected because it flowered and fruited more than most genotypes in a low latitude, zero chill evergreen production system and had large fruit with a small picking scar. 'FCM14-052' also produces significant numbers of flower buds in a zero chill climate, resulting in a concentrated harvest window.

9 Drawing Sheets

Latin name of the genus, and species:
Genus—*Vaccinium.*
Species—*corymbosum.*
Variety denomination: The new blueberry plant claimed is of the variety denominated 'FCM14-052'.

STATEMENT REGARDING FEDERALLY-SPONSORED RESEARCH AND DEVELOPMENT

None.

BACKGROUND OF THE INVENTION

The present invention relates to the discovery of a new and distinct cultivar of southern highbush blueberry (*Vaccinium corymbosum* L. hybrid) plant, referred to as 'FCM14-052', as herein described and illustrated. The new blueberry plant variety 'FCM14-052' was evaluated in Tala City, state of Jalisco, Mexico. 'FCM14-052' is a commercial variety intended for the hand harvest fresh market. The variety has medium-high vigor, ripens in a more concentrated manner at the same time as the variety 'Biloxi', and produces a medium to large berry with good firmness, and a small picking scar on fruit derived from the current season's growth. 'FCM14-052' was selected for use in an evergreen production system in areas where zero effective chilling hours may be accumulated. The growing region of Jalisco, Mexico where 'FCM14-052' was originally selected is located at 20° 39'40" N, 103° 4'35" O, 1310 meters above sea level. In this region, temperatures range from 43° F. to 92° F. and are rarely below 36° F., and day lengths only vary from between 10.8 hours in December to 13.2 hours in June. Under these conditions, many traditional low-chill, blueberry varieties (developed in latitudes 25°-35°) do not produce flower buds or flowers. In the case of blueberry varieties that do flower under these conditions, the flowers are produced primarily on the current season's growth that is often referred to as a 'primocane' in the blueberry industry. The 'primocane' inflorescences tend to be very elongated in form compared to the inflorescence produced at higher latitudes from dormant buds, and the fruit often does not abscise well from the pedicel, resulting in a large picking scar which greatly limits shelf life. The blueberry industry in this area is dominated by the variety 'Biloxi' (not patented). 'Biloxi' is one of the few traditional low chill varieties that grows well and produces fruit with a good picking scar in this growing environment. However, 'Biloxi' often produces an excessive proportion of small, unmarketable fruit. 'FCM14-052' was exceptional because of its firm, mildly aromatic sweet flavored, large fruits with a small picking scar. 'FCM14-052' also produces significant numbers of flower buds in a zero chill climate, resulting in a harvest window that is more concentrated than 'Biloxi', which fruits more heavily on prirnocanes.

SUMMARY OF THE INVENTION

Pedigree and History: The new blueberry plant originated from a cross of 'FL01-06' (female parent, unpatented) by 'FL06-556' (pollen parent, U.S. Plant Pat. No. 27,771).

The cross that produced 'FCM14-052' (denominated by the cross code 'XI2-106') was made in Lowell, Oreg., USA in 2012.

In 2013, seedlings resulting from the above-referenced cross were planted at Tala, Jalisco, Mexico and in December of 2013 evaluation for fruit production and quality of these planted seedlings began. The new blueberry plant variety 'FCM14-052' was selected in 2014 because of its good fruit quality and its very concentrated ripening period in an evergreen, zero chill production system and was initially propagated by softwood cuttings in 2014 in Tala, Jalisco, Mexico.

After 'FCM14-052' was selected and propagated by softwood cutting, two plots of 5 plants per plot were established in Tala, Mexico (near Guadalajara) during the summer of 2015. The five-plant plots were evaluated for fruit quality and yield in comparison to the standard varieties 'Biloxi' (not patented) and 'Ventura' (U.S. Plant Pat. No. 24,606) beginning in December 2015. Rooted plants from the initial softwood cutting propagation were shipped to Lowell, Oreg., USA in 2016 and were successfully used to establish in vitro culture lines in 2017 in Lowell, Oreg. After three harvest seasons of evaluation from December 2015, the yield and fruit quality of 'FCM14-052' were deemed sufficiently good to warrant launching it as a commercial variety The new blueberry plant 'FCM14-052' as it grows in Tata, Mexico is distinguished by a medium branched growth habit, with wide spaced internodes, and highly evergreen leaves resulting in a vase-shaped plant. The new blueberry plant 'FCM14-052' has new leaves that are often reddish-orange in hue and elliptic shape, urceolate flowers, and firm, large fruit with a moderately dark color and flattened shape. The new blueberry plant 'FCM14-052' consistently produces firmer fruit than the standard variety 'Biloxi' (not patented), which is a very desirable characteristic.

Plants of 'FCM14-052' propagated from softwood cuttings in Tala, Mexico or in vitro in Lowell, Oreg. are phenotypically stable and exhibit the same characteristics as the original plant. The parents 'FL01-06' (not patented) and 'FL06-556' (U.S. Plant Pat. No. 27,771) have not been evaluated in the same environment of Mexico that 'FCM14-052' was selected in. In California, USA 'FL01-06' was discarded after one season of evaluation because it did not grow well there. Very few other notes of the parent 'FL01-06' (not patented) exist, except the original selection notes for it from Lowell, Oreg., where it was noted that it had a concentrated ripening period and firm fruit. The parent 'FL06-556' has been much more extensively evaluated. The parent 'FL06-556' is similar to the new blueberry plant 'FCM14-052' in that it is very evergreen, with a medium branched growth habit and intermedia internodes. However, the leaves of 'FCM14-052' are much more rounded at the apex than leaves of the parent 'FL06-556' which have an acute apex. The fruit of 'FCM14-052' is similar in shape to the parent 'FL06-556' but fruit of 'FL06-556' have a much heavier bloom resulting a lighter blue color than 'FCM14-052'.

DETAILED BOTANICAL DESCRIPTION

Figure 1:
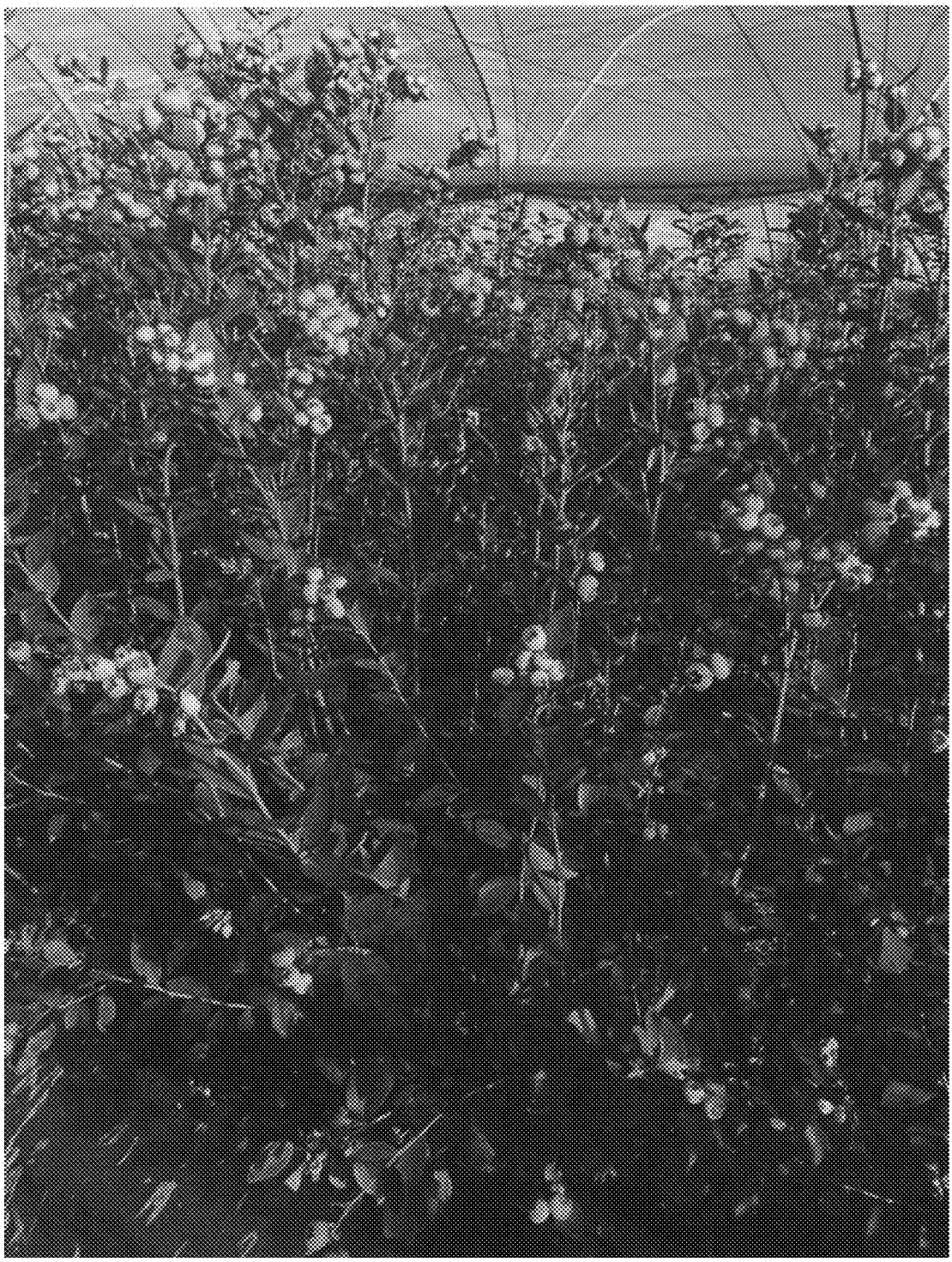
FIG. 1 depicts a mature plant of 'FCM14-052' grown in Tala, Jalisco, Mexico and photographed on Oct. 2, 2017.
Figure 2:
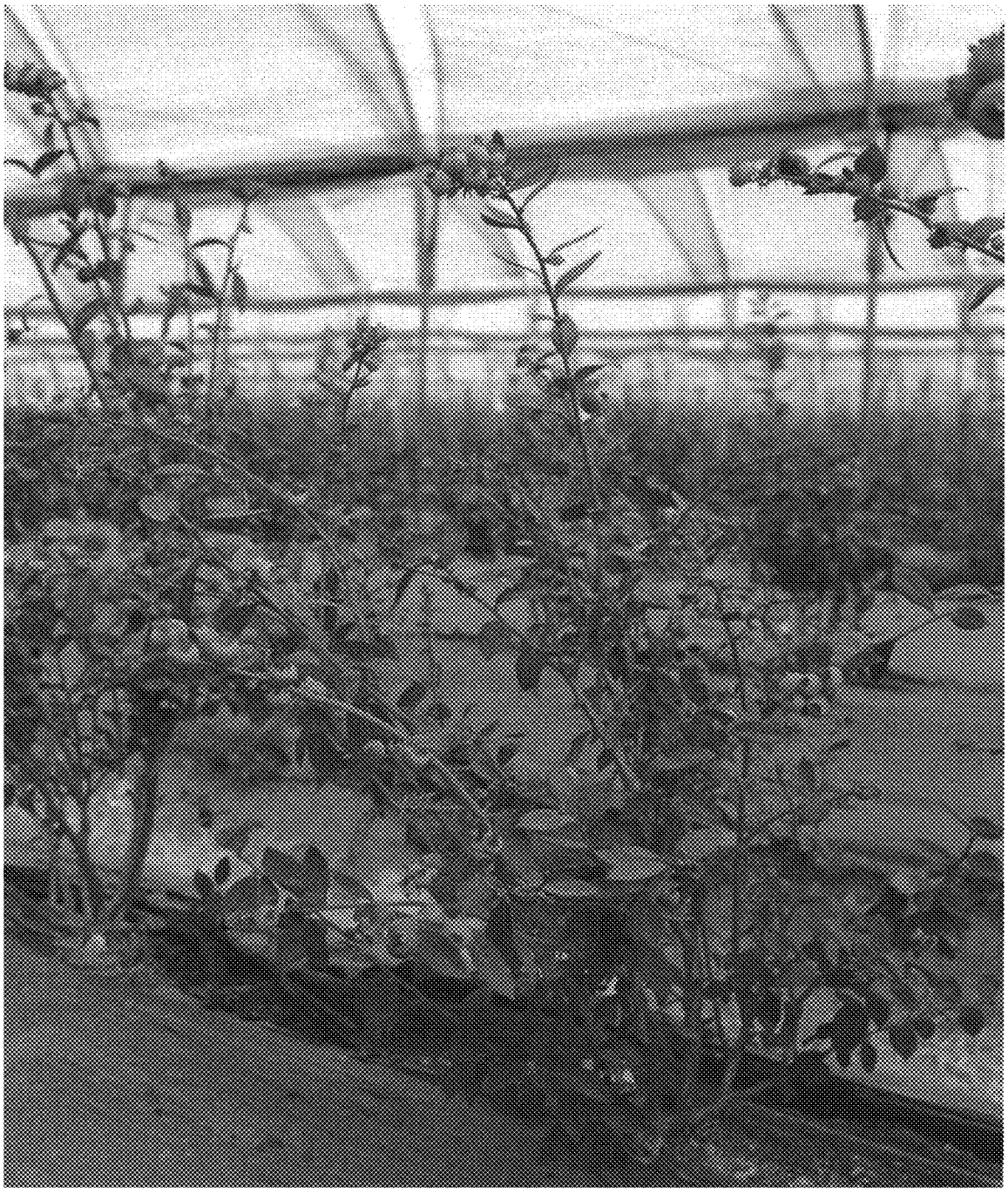
FIG. 2 depicts a young plant of 'FCM14-052' grown Tala, Jalisco, Mexico and photographed on Mar. 21, 2016.
Figure 3:
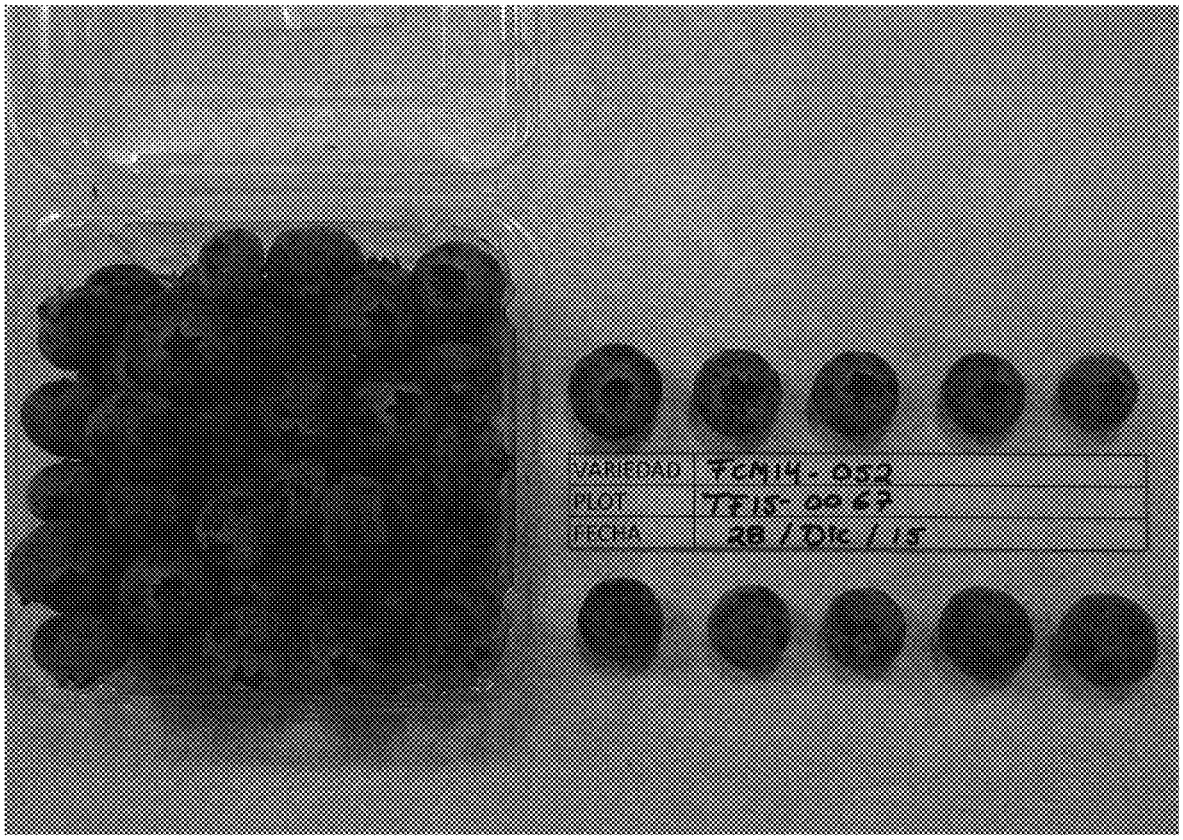
FIG. 3 depicts fruit of 'FCM14-052' grown in Tala, Jalisco, Mexico photographed on Dec. 28, 2015.
Figure 4:
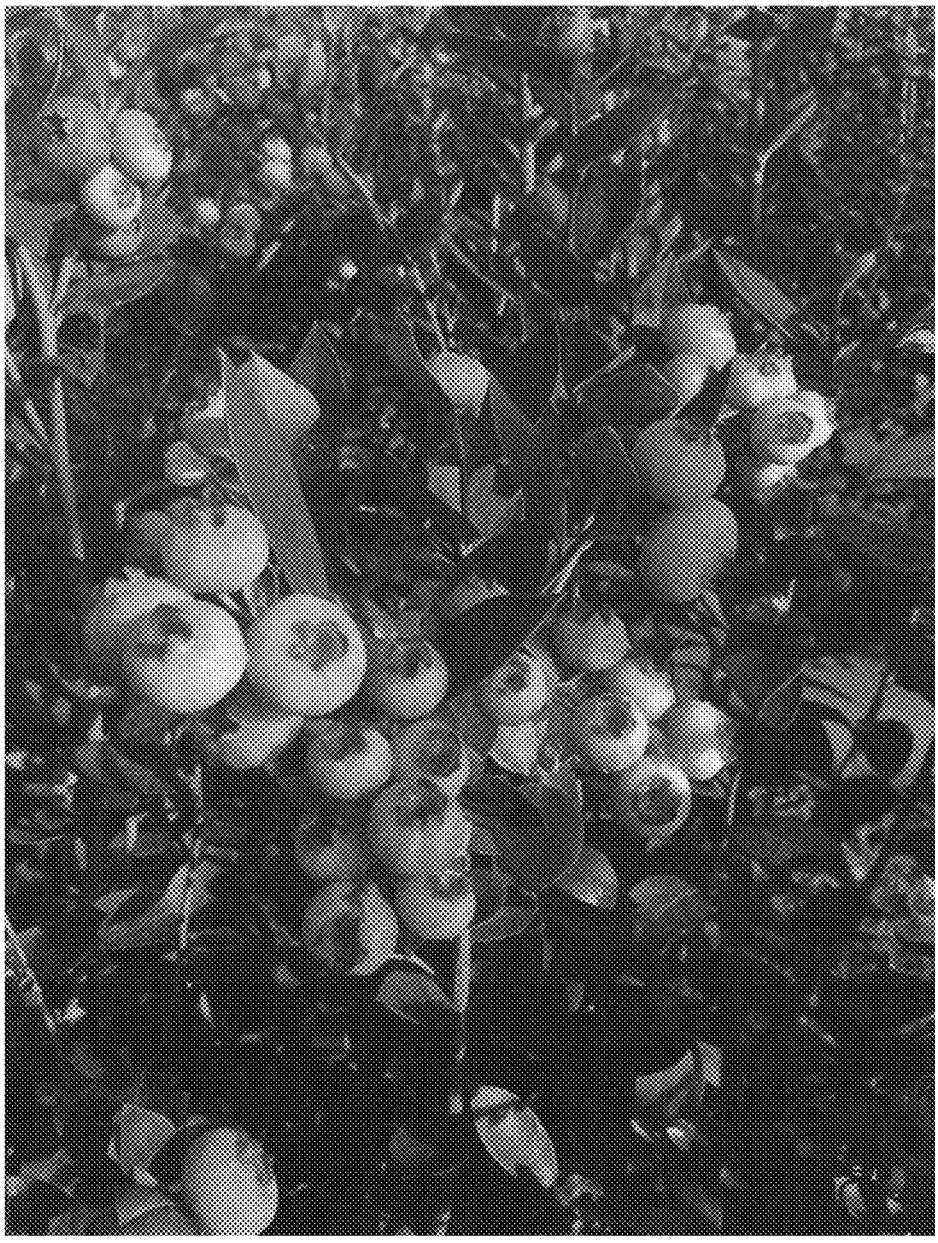
FIG. 4 depicts early fruit clusters of 'FCM14-052' grown in Tala, Jalisco, Mexico and photographed on Oct. 2, 2017.
Figure 5:
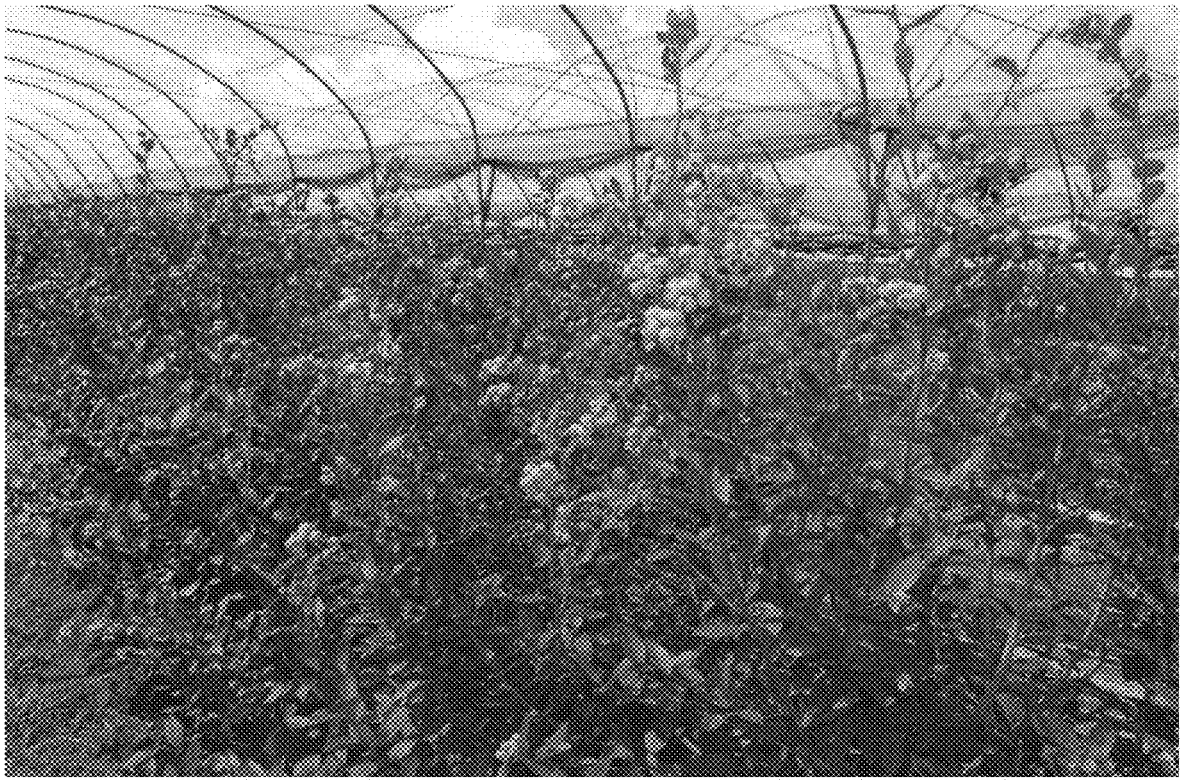
FIG. 5 depicts a mature plant of 'FCM14-052' grown in Tala, Jalisco, Mexico and photographed on Sep. 26, 2018.
Figure 6:
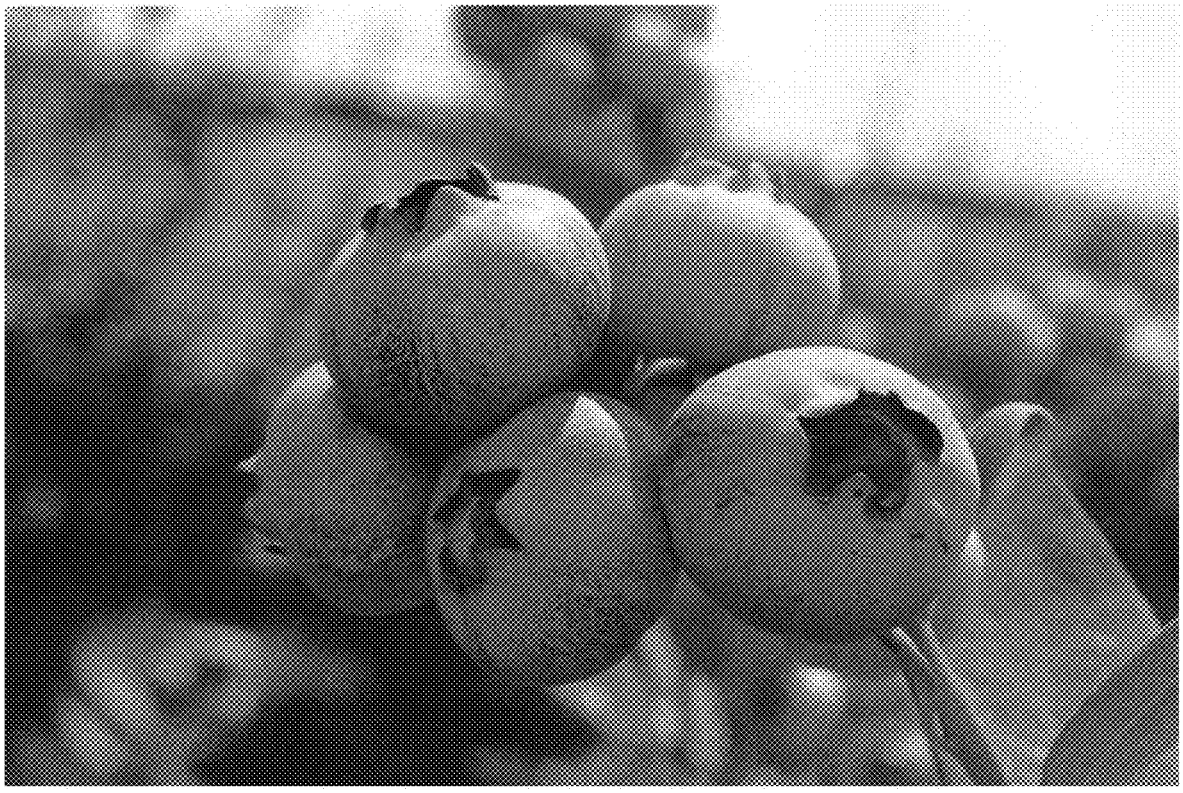
FIG. 6 depicts an early fruit cluster of 'FCM14-052' grown in Tala, Jalisco, Mexico and photographed on Sep. 26, 2018.
Figure 7:
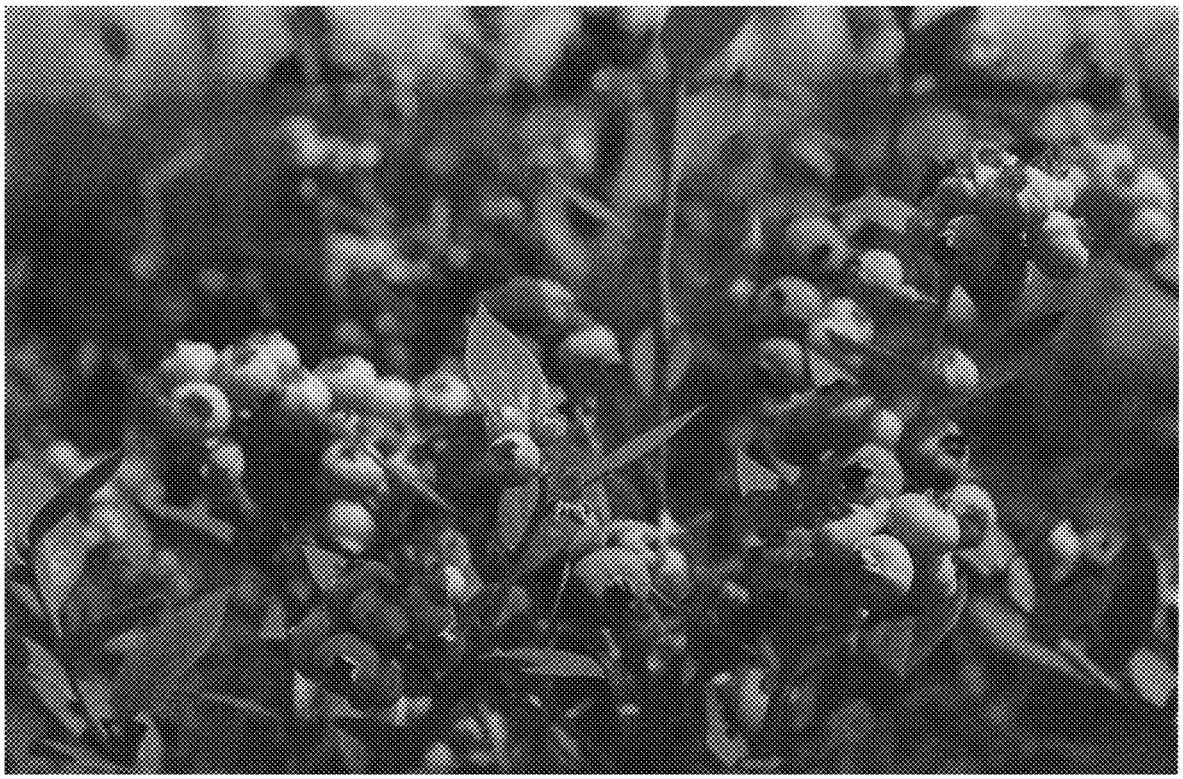
FIG. 7 depicts a budding plant with early fruit clusters of 'FCM14-052' grown in Tala, Jalisco, Mexico and photographed on Sep. 26, 2018.
Figure 8:
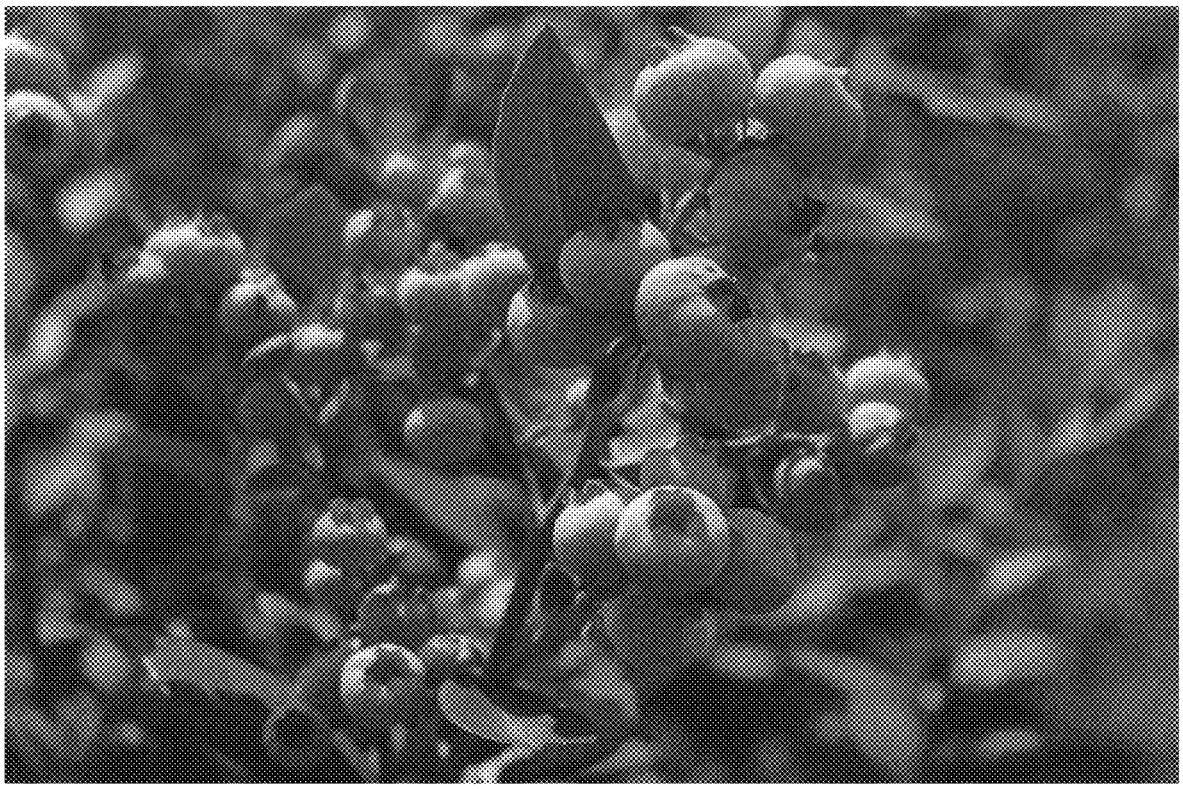
FIG. 8 depicts early fruit clusters of 'FCM14-052' grown in Tala, Jalisco, Mexico and photographed on Sep. 26, 2018.
Figure 9:
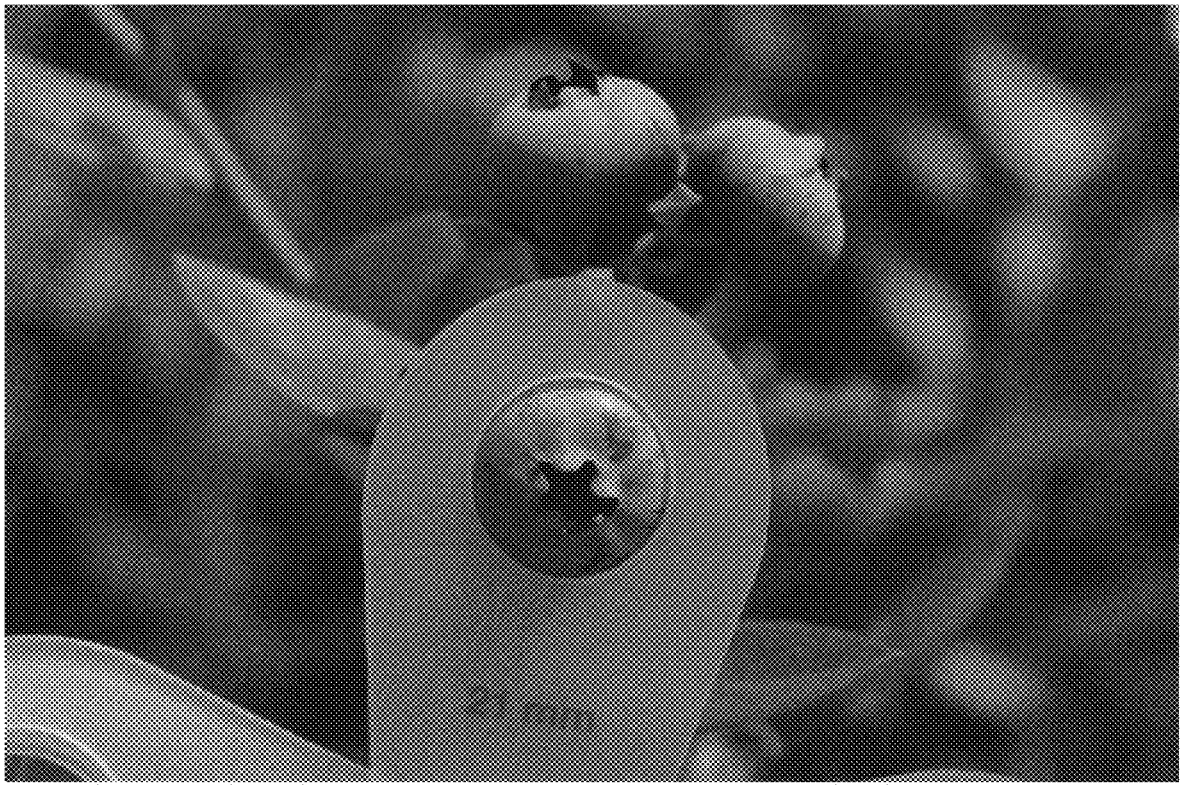
FIG. 9 depicts fruit of 'FCM14-052' grown in Tala, Jalisco, Mexico and photographed on Sep. 26, 2018.

The following detailed description sets forth the distinctive characteristics of 'FCM14-052'. The data which define these characteristics were collected from asexual reproductions of the original selection. Dimensions, sizes, colors, and other characteristics are approximations and averages set forth as accurately as possible. All measurements are the average of five observations. The plant history was taken on mature plants approximately 2 years of age, and the descriptions relate to plants grown in the field in Tala, state of Jalisco, Mexico unless otherwise noted (observations on fall leaf color and some other traits were collected on plants grown in Lowell, Oreg.). Descriptions of fruit characteristics were made on fruit grown in Tala, State of Jalisco, Mexico. Color designations are from "The Pantone Book of Color" (by Leatrice Eiseman and Lawrence Herbery, Harry N. Abrams, Inc., Publishers, New York 1990) unless noted otherwise. Where the Pantone color designations differ from the colors in the photographs, the Pantone colors are accurate.

VARIETY

Classification:

a. *Family*.—Ericaceae.

b. *Genus*.—*Vaccinium*.

c. *Species*.—*Corymbosum*.

d. *Common name*.—Southern Highbush Blueberry.

Parentage:

a. *Female parent*.—'FL01-06' (not patented).

b. *Male parent*.—'FL06-556' (U.S. Plant Pat. No. 27,771).

Market class: Commercial blueberry variety intended for the hand harvest fresh market.

PLANT

General:

a. *Parentage*.—Female parent 'FL01-06' (not patented) Male parent 'FL06-556' (U.S. Plant Pat. No. 27,771).
b. *Plant height*.—Average of 132.8 cm.
c. *Plant width*.—Average of 127.4 cm.
d. *Growth habit*.—Round.
e. *Growth*.—Vigorous.
f. *Productivity*.—Medium, average of 2.1 kilos per plant, per season on a 2 year old plant, compared to 1.86 kilos per plant per season for the commercial variety 'Biloxi' (not patented).
g. *Cold hardiness*.—Not determined, likely USDA zone 7 given southern highbush parentage.
h. *Chilling requirement*.—Not determined, estimated at less than 400 hours less than 45 degrees Fahrenheit. Capable of fruiting well with zero chill hours when maintained in an evergreen state of growth.
i. *Leafing*.—Excellent leafing.
j. *Twigginess*.—Medium.
k. *Resistance/susceptibility to root rot* (*phytopthora cinnamomii*).—Does not appear to be overly susceptible.
l. *Resistance/susceptibility to stem blight* (*botryosphaeria sp*.).—Does not appear to be overly susceptible.
m. *Resistance/susceptibility to phomopsis twig blight* (*Phomopsis vaccinii*).—Not evaluated.
n. *Resistance/susceptibility to botrytis* (*botrytis cinerea*).—Does not appear to be overly susceptible.
o. *Resistance/susceptibility to leaf spot* (*septoria spp*.).—Does not appear to be overly susceptible.
p. *Resistance/susceptibility to leaf rust* (*naohidemyces vaccinii*).—Moderately susceptible to leaf rust.
q. *Resistance/susceptibility to bud mites* (*acalatus vaccinii*).—Not evaluated.

STEM

General:

a. *Suckering tendency*.—Medium.
b. *Mature cane color*.—Pantone color Maple Sugar 15-1316.
c. *Mature cane length*.—Average of 109.4 cm.
d. *Mature cane width*.—Average of 20.5 mm.
e. *Bark texture*.—Rough.
f. *Fall color on new shoots*.—Pantone color Forest Green 17-0230.
g. *Surface texture of new wood*.—Smooth.
h. *Internode length on strong, new shoots*.—Average of 24.1 mm.
i. *Average number of buds per fruiting lateral*.—Average of 6.4.

FOLIAGE

General:

a. *Time of beginning of leaf bud burst*.—Not observed in Tala, Mexico. In Lowell, Oreg., late February to early March.
b. *Leaf color* (*top side*).—Pantone color Black Forest 19-0315.
c. *Leaf color* (*under side*).—Pantone colors Mistletoe 16-0220 Fall leaf color — Pantone color Chive 19-0323.
d. *Leaf arrangement*.—Alternate.
e. *Leaf shape*.—Elliptic.
f. *Leaf margins*.—Entire.
g. *Leaf venation*.—Anastomosing.
h. *Leaf apices*.—Attenuate.
l. *Leaf bases*.—Obtuse.
j. *Leaf length*.—Average of 61.5 mm.
k. *Leaf width*.—Average of 30.6 mm.
l. *Leaf length/width ratio*.—2.0 medium.
m. *Leaf nectaries*.—Absent.
n. *Pubescence of upper side*.—Absent.
o. *Pubescence of lower side*.—Absent.
p. *Cross sectional profile*.—Plane.
q. *Longitudinal profile*.—Entire.
r. *Attitude*.—Ascending.

Petioles:

a. *Length*.—Average of 6.828 mm.
b. *Width*.—Average of 1.22 mm.
c. *Color*.—Pantone color Tarragon 15-0326.
d. *Surface texture*.—Smooth.

FLOWERS

General:

a. *Time of beginning of flowering*.—In Tala, Mexico approximately 110-120 days after pruning.
b. *Time of* 50% *anthesis*.—In Tala, Mexico approximately 140-150 days after priming.
c. *Flower shape*.—Urceolate.
d. *Flower fragrance*.—Faint.
e. *Immature flower color*.—Pantone color Frozen Dew 13-0513.
f. *Pollen staining*.—95% viable stained with acetocarmine red.
g. *Self-compatibility*.—Medium, 42% of self-pollinated flowers reaching maturity.

Corolla:

a. *Color*.—Pantone color Angora 12-0605.
b. *Length*.—Average of 8.26 mm.
c. *Width*.—Average of 7.32 mm.
d. *Aperture width*.—Average of 3.78 mm.
e. *Anthocyanin coloration of corolla at time of anthesis*.—In Tala, Mexico: low.
f. *Corolla ridges*.—Present, distinct.
g. *Protrusion of stigma*.—Average of 0.66 mm.

Inflorescence:

a. *Length*.—Average of 17.1 mm.
b. *Diameter*.—Average of 33.4 mm.
c. *Length of peduncle*.—Average of 15.2 mm.
d. *Surface texture of peduncle*.—Smooth.
e. *Color of peduncle*.—Pantone color Leaf Green 15-0332.
f. *Length of pedicel*.—Average of 5.1 mm.
g. *Surface texture of pedicel*.—Smooth.
h. *Color of pedicel*.—Pantone Green Oasis 15-0538.
l. *Number of flowers per cluster*.—Average of 6.6.
J. *Flower cluster density*.—Low (loose).

Calyx (with sepals):

a. *Diameter*.—Average of 5.1 mm.
b. *Color* (*sepals*).—Pantone color Mistletoe 16-0220.
c. *Calyx surface*.—Smooth.

Stamen:

a. *Length*.—Average of 5.17 mm.
b. *Number per flower*.—9.6.

c. *Filament color*.—Pantone color Green Banana 14-0434.

Pistil:

a. *Length*.—Average of 9.77 mm.

b. *Ovary color* (*exterior*).—Pantone color Forest Green 17-0230.

c. *Style*.—Length — Average of 8.98 mm.

Anther:

a. *Length*.—Average of 6.7 mm.

b. *Number*.—9.6.

c. *Color*.—Pantone colors Nugget 16-1148 & Green Banana 14-0434.

Pollen:

a. *Abundance*.—Abundant.

b. *Color*.—Pantone color Cornsilk 13-0932.

FRUIT

General:

a. *Time of fruit ripening*.—Approximately October 15 in Tala, Mexico, depending on timing of previous pruning.

b. *Time of* 50% *maturity*.—Approximately October 31 in Tala, Mexico, depending on timing of previous pruning. In Lowell, Oreg.: June 12.

c. *Fruit development period*.—Approximately 60 days from fruit set to ripe.

d. *Mean harvest date*.—Approximately December 25 in Tala, Mexico when plants were pruned the previous June. Dependent on timing of previous pruning.

e. *Mean date last pick*.—Last pick occurred on approximately January 1 in Tala, Mexico. Dependent on timing of previous pruning.

f. *Cluster density*.—Medium.

g. *Berries per cluster*.—Average of 7.

h. *Unripe fruit color*.—Pantone color Lettuce Green 13-0324.

i. *Ripe berry color*.—Pantone color Lavender Gray 17-3910.

j. *Berry skin color after polishing*.—Pantone color Ebony 19-4104.

k. *Berry surface wax abundance*.—Medium-low.

l. *Berry flesh color*.—Pantone color hemp 14-0721.

m. *Berry weight*.—Average of 3.6 g per berry.

n. *Berry height from calyx to scar*.—Average of 15.55 mm.

o. *Berry diameter*.—Average of 19.73 mm.

p. *Calyx aperture*.—Average of 8.46 mm.

q. *Calyx depth*.—Average of 0.37 mm.

r. *Pedicel length*.—Average of 6.83 mm.

s. *Pedicel surface texture*.—Smooth.

t. *Berry detachment force*.—Medium, 1.5 Newtons.

u. *Berry shape*.—Oblate.

v. *Fruit stem scar*.—Small, dry.

w. *Berry flavor*.—Mild aromatic, sweet with low acidity.

x. *Sweetness when ripe*.—Medium-high.

y. *Firmness when ripe*.—Very firm, 181.56 gr/mm.

(1) *Acidity when ripe*.—Medium-low, 1.132.

(2) *Storage quality*.—Good.

(3) *Suitability for mechanical harvesting*.—Not well suited.

(4) *Self-fruitfulness*.—High.

(5) *Uses*.—Fresh market fruit production.

SEED

General:

a. *Seed abundance in fruit*.—Medium, From 3 to 10 seeds per fruit under bad pollination and controlled cross.

b. *Seed color*.—Pantone color Biscuit 16-336.

c. *Seed dry weight*.—Average 0.41 mg.

d. *Seed length*.—Average of 2.03 mm.

COMPARISON BETWEEN PARENTAL AND COMMERCIAL CULTIVARS

TABLE 1

Comparison Table

| Denomination of similar variety | Characteristic for comparison | State of expression of similar variety | State of expression of candidate variety 'FCM14-052' |
|---|---|---|---|
| 'Biloxi' (not patented) | Concentration of production | Very extended | Concentrated |
| 'Biloxi' | Yield | High | Medium |
| 'Biloxi' | Fruit firmness | Medium | Very firm |
| 'Biloxi' | Plant vigor | Very vigorous | Vigorous |
| 'Biloxi' | Fruit size | Small | Medium-Large |
| 'Biloxi' | Fruit color | Light blue | Medium light or medium dark blue |

The invention claimed is:

1. A new and distinct variety of blueberry plant named 'FCM14-052' substantially as illustrated and described herein.

* * * * *